US006231660B1

(12) United States Patent
Welshimer et al.

(10) Patent No.: US 6,231,660 B1
(45) Date of Patent: May 15, 2001

(54) MANUFACTURED GRANULAR SUBSTRATE AND METHOD FOR PRODUCING THE SAME

(75) Inventors: James W. Welshimer; David L. Ashworth; Peter V. Cawlfield; Nadine C. Dunn, all of Findlay, OH (US); Gerald L. Gingrich, deceased, late of Gibsonburg, OH (US), by Sandra Gingrich, legal representative; Karissa L. Fox, Carey, OH (US); Kim W. Venable, Winston Salem, NC (US); Paul Weinstein, Findlay, OH (US); Timothy D. Birthisel, Toledo, OH (US)

(73) Assignees: The National Lime and Stone Co., Findlay, OH (US); The Andersons, Inc., Maumee, OH (US)

( * ) Notice: Subject to any disclaimer, the term of this patent is extended or adjusted under 35 U.S.C. 154(b) by 0 days.

(21) Appl. No.: 09/342,441

(22) Filed: Jun. 29, 1999

Related U.S. Application Data

(63) Continuation-in-part of application No. 08/995,674, filed on Dec. 22, 1997, now abandoned.

(51) Int. Cl.[7] .............................. C04B 2/00; C04B 2/02; C09C 1/00; C09G 1/02

(52) U.S. Cl. .................... 106/405; 106/406; 106/407; 106/463; 106/464; 106/470; 106/481

(58) Field of Search ................................... 106/405, 406, 106/407, 463, 464, 469, 470, 481, 482, 485, DIG. 1

(56) References Cited

U.S. PATENT DOCUMENTS 4,874,786 * 10/1989 Menconi et al. ..................... 514/528
5,498,384 * 3/1996 Volk et al. ........................... 264/122

* cited by examiner

*Primary Examiner*—Mark L. Bell
*Assistant Examiner*—Michael J. DiVerdi
(74) *Attorney, Agent, or Firm*—Marshall & Melhorn

(57) ABSTRACT

A manufactured granular substrate composition suitable for use as a carrier for active chemical agents. The composition includes about 65 wt % or more of one or more mineral components having a bulk density greater than about 70 pounds per cubic foot. The composition also contains about 5 wt % to about 25 wt % of one or more light weight additives and up to 20 wt % of one or more water soluble binders. The resulting manufactured granular substrate is readily dispersable in water and has a bulk density of less than about 55 pounds per cubic foot with a size guide number of about 100 to about 230.

19 Claims, No Drawings

MANUFACTURED GRANULAR SUBSTRATE AND METHOD FOR PRODUCING THE SAME

RELATED APPLICATIONS

This application is a continuation-in-part of application Ser. No. 08/995,674, filed on Dec. 22, 1997, now abandoned. The application Ser. No. 08/995,674 is incorporated herein by reference.

BACKGROUND OF THE INVENTION

This invention relates to a manufactured granular substrate suitable for use as a carrier for chemical agents, as well as a method for producing a granular substrate. More particularly, this invention relates to a water dispersable, light weight manufactured granular substrate.

Generally, manufactured granular substrates are utilized as carriers for active chemical agents, such as for example herbicides or other pesticides. The carriers, with the active chemical agents, are utilized to distribute the active agent over a broad area. The carriers are generally inert compounds that, upon application, break down over time. Existing water dispersable carrier compositions have larger than desired particles sizes accompanied by high bulk densities of greater than 60 pounds per cubic foot. It is preferable to utilize a carrier with smaller granules and a lower bulk density in order to efficiently transport and distribute the required amount of active chemical agent without utilizing excessive amounts of inert carrier compounds.

In addition, conventional manufactured granular substrates often have a tendency to break apart thus creating handling and distribution problems. Granular substrates that resist attrition are preferred because they will not degrade and therefore maintain their particle size during handling. While resistance to attrition is important, the carrier compound must however breakdown or disintegrate upon exposure to water.

U.S. Pat. No. 5,078,779 discloses a binder composition for the granulation of dry, stable, particulate fertilizers. The composition generally includes a reactive carbonate and a reactive sulfate, in combination with a silicate strengthening agent and a water dispersing agent. Dolomite is disclosed as a carbonate source for the binder composition. The binder is used in conjunction with ammonium sulfate to provide a granulated fertilizer. In order to form the granulated fertilizer, the patent teaches the use of a reactive acid to initiate a reaction between the sulfate salt and the metal ion of the carbonate to form a complex salt.

A manufactured granular substrate having 10% to 100% plant fiber and 0% to 90% of a mineral filler is disclosed in U.S. Pat. No. 5,019,564. The substrate is formed by the agitated agglomeration of a fibrous slurry without the use of a binder. The plant fibers are generally 1 mm to 10 mm in length. The resulting substrate has a bulk density of about 20 to 42 pounds per cubic foot. The substrate is utilized as a carrier for active chemical agents. However, the substrate does not readily breakdown upon exposure to water. Additionally, the fibrous nature of the substrate can reduce the ability of the substrate to flow in bulk form.

U.S. Pat. Nos. 4,015,973, 4,954,134, and 5,228,895 all generally disclose the use of either limestone or dolomite in conjunction with a lignosulfonate binder in the formation of manufactured granular substrates. The agglomerated particles produced in accordance with the patents are either outside the preferred size and bulk density or are susceptible to degradation during handling.

Additionally, U.S. Pat. No. 5,242,690 discloses an inert manufactured granular substrate as a carrier for chemical agents. The granular carrier composition includes grain dust and a binder of either calcium or sodium lignosulfonate. The finished granular carrier exhibits a bulk density between 30 and 35 lbs per cubic foot.

Thus, existing manufactured granular substrates utilize either limestone or dolomite with other binding or reactive components to produce granular substrates as carriers for active chemical agents. The existing manufactured granular substrates are not of the desired size or bulk density. Also, some of the existing manufactured granular substrates have a tendency to breakdown during handling thereby changing the bulk density or creating distribution problems during application. Other granular substrates, produced from primarily plant fiber, have some desirable physical properties but fail to readily disintegrate upon exposure to water.

It would be an advantage to produce a manufactured granular substrate for use as a carrier compound for active chemical agents that has a bulk density of less than about 55 pounds per cubic foot at a relatively small particle size. A manufactured granular substrate having the noted properties is capable of delivering an appropriate amount of active chemical agent to a desired area while utilizing less inert material. Furthermore, smaller particle sizes provide a greater surface area for the chemical agent and result in an improved distribution or coverage of the desired area of application.

It would also be an advantage to produce a manufactured granular substrate that does not degrade during handling but breaks down when exposed to moisture or water. The resistance to attrition ensures the proper distribution of the active chemical agent upon application. Furthermore, the ability to disintegrate upon exposure to water is needed to provide the active chemical agent to the soil.

SUMMARY OF THE INVENTION

In accordance with the present invention, there is provided a novel manufactured granular substrate composition that is suitable for use as a carrier for active chemical agents. The present invention also includes a method for forming the manufactured granular substrate.

The manufactured granular substrate composition of the present invention includes one or more mineral components, one or more light weight additives, and one or more binders. The mineral component in the granular substrate is 65 wt % or more of at least one mineral compound, preferably selected from the group consisting of dolomite and limestone. The light weight additive is included in the substrate at about 5 wt % to about 25 wt %, and is preferably of one or more compounds selected from the group consisting of expanded silica, fly ash, hydrated lime, wheat flour, wood flour, ground wheat straw, cellulose and soy flour. The binder is included in an amount up to about 20 wt %, and may preferably be one or more materials selected from the group consisting of brewers condensed solubles, lignosulfonate, sodium carbonate lignin, cane molasses, beet syrup, beet molasses, desugared beet molasses, whey, starch, soy solubles with cane molasses or the like, hydrolyzed collagen, amino acid solutions, cellulose derivatives, or cellulose based polymer binders. Optionally, a coating, at about 1 wt % or less, may be added to the outer surface of the manufactured granular substrate.

The granular substrate of the present invention has a bulk density of less than about 55 pounds per cubic foot at a particle size guide number ranging from about 100 to about 230. The granular substrate should have a sufficiently high bulk density to provide the desired ballistics upon application of the finished product. The preferred bulk density is between 40 pounds per cubic foot and 55 pounds per cubic foot, and is most preferably greater than 42 pounds per cubic foot to about 52 pounds per cubic foot. Additionally, the substrates have a uniformity index at a minimum of 40. The particle size and bulk density are desirable properties for use of the granular substrate as a carrier for active chemical agents, such as herbicides or other pesticides. Additionally, the granular substrate resists attrition during handling but is capable of breaking down once exposed to water.

The process of the invention involves the mixing and pelletizing of the noted manufactured granular substrate composition. The mixing of the present inventive composition occurs at relatively low shear forces to prevent the degradation of the mix components. The pelletizing of the mixture composition may be accomplished through conventional pelletizing equipment such as pelletizing pans or drum granulators. The manufactured granular substrate, in pellet form, is then generally dried at a temperature of about 240° F. to about 300° F. to remove excess moisture and produce the manufactured substrate of the present invention.

It is an object of the present invention to provide a manufactured granular substrate, produced from at least one mineral component and additional additives, that has a bulk density of about 40 pounds per cubic foot to about 55 pounds per cubic foot at a particle size in accordance with particle size guide number standards of about 100 to about 230. A manufactured granular substrate having the noted characteristics is desirable for use as a carrier for chemical agents because the granular substrate, in bulk form, has a greater surface area for receiving the chemical agent while reducing the amount of inert material required for application. Additionally, the smaller particle size and lower bulk density of the present invention result in an improved distribution of active chemical agents over a specified area.

It is also an object of the present invention to provide a manufactured granular substrate that does not degrade during handling yet disintegrates upon application and exposure to water.

DETAILED DESCRIPTION OF THE PREFERRED EMBODIMENT

In accordance with the present invention, it has been discovered that a combination of specific mineral components, light weight additives, and binders results in a preferred manufactured granular substrate which is suitable for use as a carrier for active chemical agents. Additionally, the present invention involves a process for manufacturing the granular substrate.

The present invention provides a granular carrier in pellet form that has a bulk density of less than about 55 pounds per cubic foot at a nominal product sizing, in accordance with the size guide numbering system, of about 100 to about 230. The preferred bulk density is between about 40 pounds per cubic foot to about 55 pounds per cubic foot, and is most preferably greater than 42 pounds per cubic foot to about 52 pounds per cubic foot.

The manufactured substrate has an appropriate crush strength and resistance to attrition to prevent significant degradation of the substrate during handling. Additionally, the manufactured granular substrate quickly disperses when exposed to water. The granular substrate also has the appropriate spherocity, absorption, and solubility to enable the use of the substrate as a carrier for active chemical agents such as herbicides or other pesticides.

The manufactured granular substrate of the present invention includes one or more mineral components preferably selected from the group consisting of dolomite and limestone. The mineral components make up about 65 wt % or more of the manufactured granular substrate. In general, the mineral components have a sizing of 100% passing through a 30 mesh screen and 50% or more passing through a 200 mesh screen. The mineral components have a preferred sizing of about 100% through a 50 mesh screen and 80% or more through a 200 mesh screen. The noted mesh sizes and all those mentioned hereafter conform with U.S. standard sieve sizes. Additionally, the mineral components have a bulk density of greater than about 70 pounds per cubic foot, and preferably have a bulk density of about 75 to about 90 pounds per cubic foot. The sizing of the mineral components may vary with respect to other ingredients utilized in the agglomerated substrate. In addition to the preferred mineral components, other stone or mineral dust compounds conforming with the size and bulk density parameters may be suitable for use with the present invention.

One or more light weight additives are utilized with the present inventive composition to obtain the desired bulk density of the finished substrate. The manufactured granular substrates include about 5 wt % to about 25 wt % of the additives. The light weight additives are generally inert compounds having a bulk density of less than 35 pounds per cubic foot and a sizing of at least 20% passing through a 40 mesh screen. It is preferred that the additives have a sizing of 100% passing through a 40 mesh screen. Additionally, the light weight material should be a non-fibrous material as indicated by the sizing parameters. Fibrous material can adversely impact the dispersability and the flow characteristics of the finished granular substrate. The light weight additives are preferably selected from the group consisting of expanded silica, fly ash, hydrated lime, wheat flour, wood flour, ground wheat straw, cellulose and soy flour. However, other inert compounds meeting the bulk density and sizing specifications may be suitable for use in the present inventive composition.

A preferred embodiment includes the use of wood flour resulting from finely milled wood particle board. The wood particle board contains approximately 10 wt % of a urea-formaldehyde resin. Another preferred embodiment includes the use of wheat straw flour resulting from finely milled wheat straw particle board. The wheat straw particle board contains a diphenylmethane diisocyanate resin. In both cases, the additional resin assists in producing a granular substrate that does not degrade during handling but breaks down upon exposure to water.

A binder is utilized to agglomerate the ingredients of the present invention. The binder is utilized at an amount up to about 20 wt % (dry basis) of the granular composition. The preferred amount of binder is generally 2 wt % to 20 wt %. The binder utilized will bind the ingredients into a granular substrate which resists attrition, will not degrade and therefore maintain their particle size during handling. The binder must be such that the resulting granular substrate has a resistance to attrition (RTA) value, in accordance with ASTM E 728-91 Volume 11.04, of at least 85%. In addition, the selected binder needs to be sufficiently water soluble that the resulting granular substrate disperses quickly in water.

The binder is preferably selected from the group consisting of brewers condensed solubles, lignosulfonate, sodium carbonate lignin, cane molasses, beet syrup, beet molasses, desugared beet molasses, whey, starch, soy solubles with cane molasses or the like, hydrolyzed collagen, amino acid solutions, cellulose derivatives, or cellulose based polymer binders. Other water soluble binders having equivalent properties to, for example, the brewers condensed solubles, may be suitable for use in the present inventive composition, although economics may mitigate against their use.

The binder is generally added to the composition as a solution. The solution is typically provided as a water based slurry having about 40% to 50% solids by weight and weighing about 10 pounds per gallon. The binder may also be added and mixed with the other dry ingredients, subsequently mixing in an amount of water.

Optionally, a coating may be included with the manufactured granular substrate to provide a harder outer shell. The coating is generally added to the composition at 1 wt % or less. The coating material is added directly to the dried, finished pellets and enhances the strength of the granular substrate to prevent degradation. The preferred coating material is polyvinyl alcohol. However, other coating compositions capable of strengthening the substrate without adversely affecting the desired properties are suitable for use with the present invention.

The composition of the present invention is generally produced by first creating an admixture of the noted components within the specified ranges. The mixing of the components may occur in either a batch or continuous mixing process. Conventional mixing devices are suitable for use with the present invention. The components should be thoroughly mixed at conditions which prevent degradation or compaction of the materials. During the mixing step, the binder composition is generally added to the mixture as a solution. Optionally, at least part of the water soluble binder may be added to the pelletizing apparatus during pelletizing. Additional water, up to about 15% by weight, may be necessary for agglomeration of the materials in the inventive composition.

The admixture is then fed into a pelletizing apparatus to produce the manufactured granular substrate of the present invention. Conventional pelletizing equipment is suitable for use in producing the substrate in pellet form. The preferred pelletizing equipment is a pelletizing pan. Additionally, drum granulators or other types of granulation equipment may be used to produce the granular substrate of the present invention.

Water may be added to the mixture during the pelletizing step of the process to assist in granulation of the material. The water is generally added at an amount which results in no greater than 35% by weight in the substrate.

In accordance with the present invention, the operation of a pelletizing pan may vary with the specific formulation or ingredients in order to produce a granular substrate with the preferred properties. For example, feed rates and locations of the admixture or the water, the angle of the pan, the speed of rotation of the disc, or the depth of the pan may be varied to produce the desired product. One skilled in the art of pelletizing is capable of recognizing the variables and making adjustments to obtain the granular substrate in pellet form.

The manufactured granular substrate is then dried to a temperature of about 240° F. to about 300° F. to remove excess water utilized during the agglomeration of the components. The pellet is dried to a total moisture content of 8% or less in accordance with ASTM standard D 5033 Volume 11.04. The substrates have a preferred total moisture content of 2.0% or less. The upper temperature limitation during the drying step prevents the degradation or burning of the organic binder in the granular substrate. The substrates may be dried in conventional drying units such as for example a fluid bed dryer or a rotary dryer.

The resulting granular substrates are then screened to remove oversized and undersized granular substrates. The improperly sized material may be recycled to the mixing stage or milled to the appropriate size and rescreened. Optionally, the finished product may be sprayed with a light weight mineral oil to prevent dusting of the product in bulk form.

The sizing and bulk density are important finished product specification for the present invention. The composition of the present invention results in a relatively low bulk density while having a smaller particle size distribution. This is contrary to conventional, mineral based granular substrates, where typically larger particles have bulk densities in excess of 60 pounds per cubic foot. The resulting manufactured granular substrates of the present invention have a bulk density, as measured by ASTM E 727 Volume 11.04 standards, of less than about 55 pounds per cubic foot, and preferably from about 40 pounds per cubic foot to about 55 pounds per cubic foot.

The size of particles is determined by the size guide number/uniformity index system used in the fertilizer industry. The substrates of the present invention have a size guide number between 100 and 230 and a uniformity index of at least 40. The size guide number describes the relative particle size and is obtained by multiplying the average particle size, in millimeters, by 100. The uniformity index is a comparison of large particles to small particles. The index is expressed as a whole number between 1 and 100 with higher numbers indicating better uniformity and tighter size range. Additionally, the sizing may be determined in accordance with ASTM E 728-91 Volume 11.04 wherein the sizing is preferably 20% or more passing through a 14 mesh screen and retained on a 40 mesh screen.

The manufactured granular substrate must be strong enough so that the particle does not degrade during normal conveying and handling operations. The degradation of granular substrates would result in an increase in fine material which in turn would increase the bulk density. Additionally, dust or powder material absorbs more chemical agent and therefore would result in the improper distribution of the active chemical agent upon application.

It is preferred that the granular substrate not degrade until subject to water. However, it is also equally important that the substrate not degrade with high humidity. The ability of the granular substrate of the present invention to degrade with water is generally measured in a water dispersability test. The test involves placing about 10 grams of the granular substrate into 100 ml of water at room temperature in a closed glass container. The container is then inverted and the time is observed until the material completely disperses. After every minute, the container is inverted. The granular substrate of the present invention has a dispersability time of generally less than 3 minutes.

The strength of the granular substrate is determined through the crush strength test, ASTM E 382 Volume 3.06, and resistance to attrition (RTA) test, ASTM E 728-91 Volume 11.04. The manufactured granular substrate of the present invention has a crush strength between 2 and 8 pounds on an 8 mesh pellet. Additionally, the granular substrate has an RTA value of at least 85%.

The resulting granular substrate of the present invention generally has a smooth surface and is spherical in shape. The spherocity lends to desired flow characteristics of the substrates in bulk form. The angle of repose is a test utilized to measure the ability of a substrate to flow in bulk form. The test is conducted on a 14×30 mesh sample. The granular substrates of the present invention all have an angle of repose of 35 degrees or less.

The granular substrate must have the capability of absorbing the active chemical agent in order to function as a carrier. The active agent is generally absorbed in the carrier up to about five percent by weight. The substrate is also water soluble and therefore degrades upon exposure to moisture or water.

The manufactured granular substrate of the present invention is suitable for use as a carrier for active chemical agents. For example, active chemical agents could include herbicides or other pesticides that are commonly distributed through the use of a carrier in bulk form.

The following examples, which constitute the best mode presently contemplated by the inventors for practicing the present invention, are presented solely for the purpose of further illustrating and disclosing the present invention, and are not to be construed as a limitation on the invention:

EXAMPLES 1–7

A series of examples were produced in the lab to demonstrate the composition of the present invention. The specified dry based raw materials for each example were weighed out and placed in a Forberg type mixer made by Paul O. Abbe, Inc. Of Little Falls, N.J. The mixer was run for about one minute in order to thoroughly mix the materials before adding the binder composition. The binder composition, in solution form, was added to the materials over a one minute time period and then mixed for another minute.

The resulting wet mixture was then fed into a 36" rotating pelletizing pan through a Vibra Screw™ feeder. The feed rates to the pelletizer for each example are listed in Table I. The pan angle was 50° (from horizontal). The pan depth was maintained at 6 inches while the pan speed was 26 rpm. Additional water was sprayed into the pelletizer to assist in the agglomeration process. The substrates, in pellet form, were collected from the pelletizing pan and placed in a conventional lab oven. The granular substrates were then heated to a temperature of about 240° F. to about 300° F. to remove excess water.

The finished substrates where then tested to obtain the bulk density, particle size, crush strength, RTA, and total moisture content. The results of each sample are listed in Table I.

EXAMPLE 8

The example was produced to demonstrate the manufactured granular substrate and process of the present Invention on large scale production equipment. The noted amounts of dry ingredients were mixed in a two cubic foot Forberg type mixer for about 1 minute. The binder composition was then added to the mixing vessel and thoroughly mixed with the materials for about another minute.

The mixture was then transferred to an AccuRate™ surge hopper having a 2" feeder screw. The feeder screw was used to continuously feed the mixture to a three foot diameter pelletizing disc at a rate of 608 pounds per hour. The three foot diameter pelletizing disc utilized a 5 inch deep pan and was operated at a 56 degree (from horizontal) pan angle and a speed of 26 RPM. Additional water was introduced near the feed inlet through spray nozzles to assist in the agglomeration. Then the resulting pellets were collected from the disc outlet. The moisture content of the pellets was about 21%.

The pellets produced from the pelletizing disc were transferred to TecWeigh™ feeder surge hopper having a 3" feeder screw. The pellets were then continuously fed into a 24 inch diameter by 20 foot long rotary dryer. The granular substrates were fed into the dryer at about 1000 pounds per hour. The dryer was a co-current gas fired dryer with internal lifters and rotating at about 11 rpm. The combustion temperature in the dryer was controlled at about 1400° F. while the outlet temperature was monitored at 220° F. The outlet product temperature was controlled at about 175° F. The total moisture content of the finished pellet was less than 0.5%.

The finished product was collected and tested to obtain bulk density, particle size, crush strength, RTA, angle of repose, water dispersability, and total moisture content The results are listed in Table I.

EXAMPLE 9–12

The specified amounts of dry ingredients were mixed in a Forberg type mixer, having a four cubic foot capacity, for about one minute. For diluted binders, the binder solution was previously prepared in a 3.5 cubic foot rotary drum mixer. The binder solution was then added to the Forberg type mixer and then allowed to mix for another minute.

The mixture was transferred to a Vibra Screw™ live bin feeder having three cubic foot hopper and three inch diameter screw. The material was continuously fed into a 36" diameter disc pelletizer at a rate as indicated in Table I. For Examples 9–11, the pelletizer was operated at a pan angle of 50 degrees from horizontal and a pan speed of 26 rpm. For Example 12, the pelletizer was operated at a pan angle of 59.5 degrees (from horizontal) and a pan speed of 24 rpm.

The wet pellets were then fed into a continuous vibrating fluidized bed dryer having a 9'×1' perforated tray. The fluidized bed utilized an oscillating tray to convey the material. Hot air was blown through the perforated tray at a rate of 1400 cfm and a temperature of about 500° F. to about 550° F. The hot air was utilized to dry a 3"–4" deep bed (when fluidized) of granular substrate. For Examples 9–11, the granular substrate was fed to the fluidized bed at a rate of about 1200 pounds per hour. For Example 12, the granular substrate was fed at a rate of about 400 pounds per hour. The granular substrates were heated to a temperature of about 270° F. to 300° F.

The finished product was collected and tested to obtain bulk density, particle size, water dispersability, RTA, and total moisture content. Additionally, the angle of repose was measured for the resulting granular substrate of Example 10. The results of each sample are listed in Table I.

| EXAMPLE | 1 | 2 | 3 | 4 | 5 | 6 | 7 | 8 | 9 | 10 | 11 | 12 |
|---|---|---|---|---|---|---|---|---|---|---|---|---|
| POUNDS OF INGREDIENTS PER ~100 POUND BATCH | | | | | | | | | | | | |
| DOLOMITE | 83.2 | 83.2 | 83.2 | 83.2 | 83.2 | 83.2 | 83.2 | 83.2 | 90 | 83.2 | 83.2 | 85 |
| WHEAT FLOUR | 7.6 | 7.6 | 11.4 | 11.4 | 11.4 | 7.6 | 7.6 | 7.6 | 0 | 11.4 | 7.6 | 0 |

-continued

| EXAMPLE | 1 | 2 | 3 | 4 | 5 | 6 | 7 | 8 | 9 | 10 | 11 | 12 |
|---|---|---|---|---|---|---|---|---|---|---|---|---|
| WOOD FLOUR | 0 | 7.6 | 7.6 | 7.6 | 11.4 | 7.6 | 0 | 0 | 10 | 7.6 | 7.6 | 15 |
| FLY ASH | 0 | 0 | 0 | 0 | 0 | 0 | 7.6 | 7.6 | 0 | 0 | 0 | 0 |
| EXPANDED SILICA | 9.2 | 0 | 0 | 0 | 0 | 0 | 9.2 | 9.2 | 0 | 0 | 0 | 0 |
| LIQUID BINDERS (MILLILITER PER ~100 POUND BATCH) | | | | | | | | | | | | |
| BREWERS CONDENSED SOLUBLES | 0 | 0 | 8256 | 8256 | 0 | 8256 | 0 | 0 | 0 | 8256 | 0 | 8256 |
| LIGNOSULFONATE | 8256 | 8256 | 0 | 0 | 8751 | 0 | 8884 | 8884 | 8256 | 0 | 8256 | 0 |
| DILUTION | 18% | 18% | 0% | 10% | 18% | 0% | 10% | 10% | 18% | 0% | 18% | 0% |
| APPROX. FEED RATE TO PAN (POUNDS/HOUR) | 503 | 360 | 600 | 570 | 600 | 600 | 384 | 608 | 540 | 460 | NA | ~400 |
| WEIGHT % <14 AND >40 MESH | 21.9 | 41.7 | 39.6 | 44 | 55.7 | 37.6 | 58 | 62 | 62.5 | 32.1 | 56.3 | ~10 |
| BULK DENSITY POUNDS/CUBIC FOOT (14 × 40 MAT'L) | 47.8 | 48.8 | 49.2 | 45.2 | 41.5 | 47.1 | 47.5 | 50 | 49.9 | 48.4 | 50.9 | 46.9 |
| % RESISTANT TO ATTRITION (RTA) (14 × 40 MATERIAL) | 87.5 | 96.2 | 97.6 | 92.5 | 87.5 | 93.1 | 94.5 | 92 | 92.6 | 97 | 97.4 | 97 |
| CRUSH STRENGTH (POUNDS) (8 MESH PELLETS) | 2 | 3.1 | 3.2 | 2.5 | 2.7 | 3 | 1.5 | 2 | NA | NA | NA | NA |
| % MOISTURE DRY PELLETS | ~1.5 | ~1.5 | ~1.5 | ~1.5 | ~1.5 | ~1.5 | ~1.5 | 0.3 | 1.1 | 1.2 | 1.7 | 0.41 |
| DISPERSABILITY (MINUTES) | NA | NA | NA | NA | NA | NA | NA | <2 | ~1 | <3 | <3 | <2 |
| ANGLE OF REPOSE | NA | NA | NA | NA | NA | NA | NA | <35 | NA | 33.9 | NA | NA |

EXAMPLES 13–32

A series of examples were produced in the lab to demonstrate the use of a variety of binders in the composition of the present invention. In this series of examples, the mineral component was 82.5 pounds of #60 dry dolomite and the light weight additive was 17.5 pounds of minus 40 mesh particle wood particle flour, except for the example using the Polybind 300M™ binder, in which 80 pounds of #60 dry dolomite and 20 pounds of minus 40 mesh wood particle board flour were used. These dry based raw materials were weighed out and placed in a Forberg type mixer, having a four cubic foot capacity, made by Paul O. Abbe, Inc. of Little Falls, N.J. The mixer was run for about 30 seconds in order to thoroughly mix the dry materials before adding the specified binder composition. The binder composition, in solution form, was added to the materials over a 30 second time period and then mixed for another 30 seconds.

The resulting wet mixture was then fed into a 36" rotating pelletizing pan through an AccuRate™ volumetric feeder. The feed rates to the pelletizer for each example are listed in Table II. The pan angle was 56° (from horizontal). The pan depth was maintained at about 4.5 inches, while the pan speed was 24 rpm. Additional water was sprayed into the pelletizer to assist in the agglomeration process. The substrates, in pellet form, were collected from the pelletizing pan and placed in a Ty-Lab™ sieve shaker having several heat guns connected thereto. The Ty-Lab™ sieve shaker uses square sieves approximately 16 inches on a side. The shaker was equipped with four sieves for granular substrate conditioning—6 mesh, 8 mesh, 16 mesh, and 30 mesh. The shaker was operated to subject approximately a 4 pound batch of the granular substrates to approximately 5 vertical oscillations per second, of an amplitude of about ½ inch, for a total of from 20–40 seconds and at a temperature of about 220° F. The granular substrates were then heated to a temperature of about 240° F. to about 300° F. in a conventional lab oven to remove excess water.

The finished substrates where then tested to obtain the bulk density, particle size, RTA, water dispersability, and particle size distribution. The results of each sample are listed in Table II.

TABLE II

| Binder | Ex. | Pounds of Binder Solids Per 100 Lbs. of Dry Ingred. | Feed Rate Pnds Per Hour | Bulk Density Pounds/Cubic Foot (12 × 30 Material) | RTA | Dispersability (Minutes) | Wt. % 12 × 30 | Weight % Passing 30 |
|---|---|---|---|---|---|---|---|---|
| Brewers condensed solubles | 13 | 11.5 | 540 | 44 | 90 | 1 | 20 | 30 |
| Cane Molasses | 14 | 12 | 600 | 48 | ~91.5 | 1 | 30 | 25 |
| Cane Molasses | 15 | 8 | 360 | 52 | 87.5 | 1 | 34 | 45 |
| Cane Molasses | 16 | 6 | 400 | 47 | 86 | 1 to 2 | 33 | 55 |
| Beet Syrup | 17 | 12 | 600 | ~56 | ~94 | 1 | 30 | 30 |
| 50 cane mol./50 beet syrup | 18 | 10 | 480 | 57 | 93 | 1 | 35 | 35 |
| Beet Molasses | 19 | 12 | 900 | 50 | ~94 | 1 | 20 | 40 |
| Beet Molasses | 20 | 7 | 300 | 44 | 86 | 1 | 23 | 55 |
| Desugared Beet Mol. | 21 | 12 | 580 | ~53 | ~92 | 1 | 35 | 40 |
| Hydrolysed Collagen | 22 | 5 | 320 | ~47 | 93 | 1 | 37 | 35 |
| 75 Soy Solubles/25 Cane Mol | 23 | 12 | 550 | ~49 | ~90 | 1 | 17 | 65 |
| 60 Whey/45 Cane Mol | 24 | 12 | 500 | 51.5 | ~90 | 1 | 30 | 40 |
| 60 Whey/40 Cane Mol | 25 | 10 | 360 | 54 | 96 | 2 | 35 | 25 |

TABLE II-continued

| Binder | Ex. | Pounds of Binder Solids Per 100 Lbs. of Dry Ingred. | Feed Rate Pnds Per Hour | Bulk Density Pounds/Cubic Foot (12 × 30 Material) | RTA | Dispersability (Minutes) | Wt. % 12 × 30 | Weight % Passing 30 |
|---|---|---|---|---|---|---|---|---|
| 50 Whey/50 Cane Mol | 26 | 12 | 600 | ~50 | 95.5 | 1 | 35 | 40 |
| 50 Whey/50 Cane Mol | 27 | 10 | 400 | 55 | 88 | 1 | 30 | 40 |
| Flambinder[1] | 28 | 10 | 400 | ~48.5 | 97 | 1 | 60 | 10 |
| Flambinder | 29 | 8 | 400 | ~52 | ~94.5 | 1 | 47 | 33 |
| Polybind 300M[2] | 30 | 10.3 | 600 | ~45 | 97 | 1 | 60 | 10 |
| Cellubind 2000[3] | 31 | 10 | 300 | 49.5 | 97 | 1 | 50 | 15 |
| Polybind HC[4] | 32 | 8 | 480 | 52 | ~92 | 2 | 50 | 35 |

[1]Calcium Lignosulfonate from Fraser Papers, Inc. of Park Falls, Wisconsin.
[2]Sodium carbonate lignin from Northway Lignin Chemical of Sturgeon Falls, Ontario.
[3]By-product of grain processing with about 75 weight % crude protein amino acids, commercially available from Northway Lignin Chemical of Sturgeon Falls, Ontario.
[4]Hemi-cellulose extract commercially available from Northway Lignin Chemical of Sturgeon Falls, Ontario.

EXAMPLES 33–34

Examples 33 and 34 were produced in the lab to demonstrate the use of dry binders in the composition of the present invention. In example 33, the mineral component was 82.5 pounds of #60 dry dolomite and the light weight additive was 17.5 pounds of minus 40 mesh wood particle board flour. In example 34, the mineral component was 84 pounds of #60 dry dolomite and the light weight additive was 16 pounds of minus 40 mesh wood particle board flour. These dry based raw materials, including the specified dry binder, were weighed out and placed in a Forberg type mixer, having a four cubic foot capacity, made by Paul O. Abbe, Inc. of Little Falls, N.J. The mixer was run for about 30 seconds in order to thoroughly mix the dry materials. Twenty pounds of water was added to the dry materials over a 30 second time period and then mixed for another 30 seconds. The resulting wet mixture was then pelletized, conditioned and dried as with examples 13–34.

The finished substrates where then tested to obtain the bulk density, particle size, RTA, water dispersability (disp.), and particl size distribution. The results of each sample are listed in Table III.

The resulting wet mixture was then fed into a 36" rotating pelletizing pan through an AccuRate™ volumetric feeder. The feed rates to the pelletizer for each example are listed in Table IV. The pan angle was 56° (from horizontal). The pan depth was maintained at about 4.5 inches, while the pan speed was 24 rpm. Additional water was sprayed into the pelletizer to assist in the agglomeration process. The substrates, in pellet form, were collected from the pelletizing pan and placed in a Ty-Lab™ sieve shaker having several heat guns connected thereto. The granular substrates were conditioned in the Ty-Lab™ sieve shaker as in examples 13–32, except that for examples 35–41, an approximately 2 pound batch was shaken for about 90 seconds. The granular substrates were then heated to a temperature of about 240° F. to about 300° F. in a conventional lab oven to remove excess water.

The finished substrates where then tested to obtain the bulk density, particle size, RTA, water dispersability, and particle size distribution. The results of each sample are listed in Table IV.

TABLE III

| Binder | Ex. | Binder Solids Lbs./100 Lbs. Dry Ingred. | Feed Rate Pounds Per Hour | Bulk Density Pounds/Cubic Foot (12 × 30 Material) | RTA | Disp. (Min.) | Wt. % 12 × 30 | Weight % Passing 30 |
|---|---|---|---|---|---|---|---|---|
| Peridur[1] | 33 | 1.4 | 550 | 40 | 88 | 2 | 25 | 45 |
| 50 Peridur/50 corn starch | 34 | 2.8 | 200 | 49 | ~87 | 1 | ~50 | ~37 |

[1]Sodium carboxymethyl cellulose based, water soluble polymer, commercially available from Dreeland, Inc. of Denver, Colorado.

EXAMPLES 37–43

A series of examples were produced in the lab to demonstrate the use of a variety of light weight additives in the composition of the present invention. The samples were prepared using the specified raw materials, which were weighed out and placed in a Forberg type mixer, having a 4 cubic foot capacity, made by Paul O. Abbe, Inc. of Little Falls, N.J. The mixer was run for about 30 seconds in order to thoroughly mix the dry materials before adding the specified amount of the binder, brewers condensed solubles. The binder composition, in solution form having 4.5 pounds of solids per gallon, was added to the materials over a 30 second time period and then mixed for another 30 seconds.

TABLE IV

| Examples | 35 | 36 | 37 | 38 | 39 | 40 | 41 |
|---|---|---|---|---|---|---|---|
| #60 Dolomite, Pounds | 85 | 80 | 88 | 86.5 | 86.5 | 85 | 82.5 |
| Oak Wood Dust (−40 Grade), Pounds | 15 | 20 | 0 | 0 | 0 | 0 | 0 |
| Ground Wheat Straw, Pounds | 0 | 0 | 12 | 13.5 | 0 | 0 | 0 |
| Wood Particle Board Flour (−40 Grade), Pounds | 0 | 0 | 0 | 0 | 0 | 0 | 15 |
| Wheat Straw Particle Board Flour, Pounds | 0 | 0 | 0 | 0 | 13.5 | 15 | 0 |
| Omnicel[1], Pounds | 0 | 0 | 0 | 0 | 0 | 0 | 5 |
| Gallons of Brewer's | 2.2 | 2.2 | 3 | 3 | 2.4 | 2.5 | 0 |

TABLE IV-continued

| Examples | 35 | 36 | 37 | 38 | 39 | 40 | 41 |
|---|---|---|---|---|---|---|---|
| Condensed Solubles Per 100 Lbs. of Dry Ingredients | | | | | | | |
| Cane Molasses, Pounds of Solids Per 100 Lbs. of Dry Ingredients | 0 | 0 | 0 | 0 | 0 | 0 | 8 |
| Feed Rate Pounds Per Hour | 600 | 650 | 540 | 450 | 400 | 400 | 420 |
| Bulk Density Pounds/Cubic Foot (12 × 30 Material) | 52.6 | 47.6 | 48.8 | 54.5 | 48.4 | 47 | ~52 |
| RTA | 96 | 83 | 97 | 79 | 90.8 | 87.4 | 92.6 |
| Dispersability (Minutes) | 1 | 1 | 1 | NA | 5 | 1 | 1 |
| Weight % 12 × 30 | 48 | 43 | NA | 53.4 | 21.8 | 40 | ~46 |
| Weight % Passing 30 | 18 | 12 | NA | 27 | 1.1 | 35 | ~46 |

[1]Microcrystalline cellulose commercially available from Functional Foods of Englishtown, New Jersey.

In accordance with the provisions of the patent statutes, the present invention has been described in what is considered to represent its preferred embodiment. However, it should be noted that the invention can be practiced otherwise than as described without departing from its spirit and scope.

What is claimed is:

1. A manufactured granular substrate suitable for use as a carrier for chemical agents, comprising:
   (a) about 65 wt % or more of one or more mineral components, the one or more mineral components having a bulk density of greater than about 70 pounds per cubic foot and a sizing of about 100% passing through a 30 mesh screen and about 50% or more passing through a 200 mesh screen;
   (b) about 5 wt % to about 25 wt % of one or more light weight additives, each additive having a bulk density of less than 35 pounds per cubic foot and a sizing of at least 20% passing through a 40 mesh screen; and
   (c) about 2 wt % to about 20 wt % of one or more water soluble binders;
   the granular substrate having a bulk density of less than about 55 pounds per cubic foot.

2. A manufactured granular substrate as recited in claim 1, wherein the granular substrate has a bulk density of about 40 pounds per cubic foot to less than about 55 pounds per cubic foot.

3. A manufactured granular substrate as recited in claim 2, wherein the granular substrate has a bulk density of greater than 42 pounds per cubic foot to about 52 pounds per cubic foot.

4. A manufactured granular substrate as recited in claim 1, wherein said granular substrate has an RTA of at least 85%.

5. A manufactured granular substrate as recited in claim 1, wherein said the one or more mineral components have a bulk density of from about 75 to about 90 pounds per cubic foot.

6. A manufactured granular substrate as recited in claim 1, wherein said granular substrate has a water dispersability of about 3 minutes or less.

7. A manufactured granular substrate as recited in claim 1, wherein said granular substrate has a crush strength of 2 to 8 pounds on an 8 mesh pellet.

8. A manufactured granular substrate as recited in claim 1, wherein said granular substrate has a particle size guide number of about 100 to about 230 and a uniformity index of at least 40.

9. A manufactured granular substrate as recited in claim 1, wherein said granular substrate has a total moisture content of 8% or less.

10. A manufactured granular substrate as recited in claim 1, wherein said granular substrate has an angle of repose of 35 degrees or less.

11. A manufactured granular substrate as recited in claim 1, wherein said light weight additive is one or more of the group consisting of expanded silica, fly ash, hydrated lime, wheat flour, wood flour, ground wheat straw, cellulose and soy flour.

12. A manufactured granular substrate as recited in claim 1, wherein said light weight additive is wood flour containing an amount of urea-formaldehyde resin.

13. A manufactured granular substrate as recited in claim 1, wherein said mineral component is one or more of the group consisting of dolomite and limestone.

14. A manufactured granular substrate as recited in claim 1, wherein said mineral component is dolomite.

15. A manufactured granular substrate as recited in claim 1, wherein said water soluble binder is one or more of the group consisting of brewers condensed solubles, lignosulfonate, sodium carbonate lignin, cane molasses, beet syrup, beet molasses, desugared beet molasses, whey, starch, soy solubles with cane molasses, hydrolyzed collagen, amino acid solutions, cellulose derivatives, and cellulose based polymer binders.

16. A manufactured granular substrate as recited in claim 1, wherein said water soluble binder is comprised of brewers condensed solubles.

17. A manufactured granular substrate suitable for use as a carrier for chemical agents, comprising:
   (a) about 65 wt % or more of one or more mineral components, the one or more mineral components having a bulk density of about 75 to about 90 pounds per cubic foot and a sizing of about 100% passing through a 30 mesh screen and about 50% or more passing through a 200 mesh screen;
   (b) about 5 wt % to about 25 wt % of one or more light weight additives, each additive having a bulk density of less than 35 pounds per cubic foot and a sizing of at least 20% passing through a 40 mesh screen; and
   (c) about 2 wt % to about 20 wt % of one or more water soluble binders selected from the group consisting of brewers condensed solubles, lignosulfonate, and sodium carbonate lignin, the granular substrate having a bulk density of about 40 pounds per cubic foot to about 55 pounds per cubic foot.

18. A method of producing light weight granular substrates, comprising:
   (a) mixing about 65 wt % or more of one or more mineral components, the one or more mineral components having a bulk density greater than about 70 pounds per cubic foot and a sizing of about 100% passing through a 30 mesh screen and about 50% or more passing through a 200 mesh screen, about 5 wt % to about 25% of one or more light weight additives, each additive having a bulk density of less than 35 pounds per cubic foot and a sizing of at least 20% passing through a 40 mesh screen, and about 2 wt % to about 20 wt % of one or more water soluble binders to form a granular substrate admixture;
   (b) pelletizing said admixture to form granular substrates; and
   (c) drying said granular substrates at a temperature sufficient to remove excess moisture and produce finished granular substrates having a bulk density of less than about 55 pounds per cubic foot.

19. A method as recited in claim 18, wherein said granular substrate has a particle size guide number of about 100 to about 230 and a uniformity index of at least 40.

* * * * *

UNITED STATES PATENT AND TRADEMARK OFFICE
CERTIFICATE OF CORRECTION

PATENT NO. : 6,231,660 B1
DATED : May 15, 2001
INVENTOR(S) : Welshimer et al.

It is certified that error appears in the above-identified patent and that said Letters Patent is hereby corrected as shown below:

In the Detailed Description of the Preferred Embodiment:
<u>Beneath Columns 7 and 8 and above the Table,</u>
Insert -- Table 1 --.

<u>Columns 9 and 10</u>
Above the Table, delete "-continued" insert -- Table 1 -- continued --.

<u>Column 11,</u>
Line 36, delete "34", insert -- 32 --.
Line 53, delete "37-43", insert -- 35-41 --.

Signed and Sealed this

Twelfth Day of March, 2002

Attest:

Attesting Officer

JAMES E. ROGAN
Director of the United States Patent and Trademark Office